(12) United States Patent
Larose

(10) Patent No.: US 7,368,121 B2
(45) Date of Patent: May 6, 2008

(54) PROCESS FOR CONTROLLING MOSS AND LIVERWORT

(76) Inventor: Robert A Larose, 3 Far View Run, Marlborough, CT (US) 06447

( * ) Notice: Subject to any disclaimer, the term of this patent is extended or adjusted under 35 U.S.C. 154(b) by 0 days.

(21) Appl. No.: 11/163,114

(22) Filed: Oct. 5, 2005

(65) Prior Publication Data

US 2006/0029631 A1    Feb. 9, 2006

Related U.S. Application Data

(62) Division of application No. 10/139,164, filed on May 2, 2002, now abandoned.

(51) Int. Cl.
*A01N 25/32* (2006.01)

(52) U.S. Cl. .................. 424/405; 71/63; 423/415.2; 424/616; 424/676; 424/693; 424/694; 424/695.5; 424/715; 424/717; 424/405

(58) Field of Classification Search .................. 71/63; 423/415.2, 419.1
See application file for complete search history.

(56) References Cited

U.S. PATENT DOCUMENTS 5,639,794 A * 6/1997 Emerson et al. ............ 514/699

OTHER PUBLICATIONS

STN Registry File of CAS of Soda Ash, Nov. 16, 1984 entry.*
Hach's Chemical Dictionary P620 Sodium Percarbonates 1972.*
STN data base search of Sodium Percarbonate.*

* cited by examiner

Primary Examiner—Neil S. Levy
(74) Attorney, Agent, or Firm—Robert S. Smith

(57) ABSTRACT

A process for eradicating moss and liverwort which includes applying sodium percarbonate; and irrigating the moss. In some cases the process includes applying lime to control the pH of the moss and thereby constrain development of additional moss and said sodium percarbonate is a solid material.

20 Claims, No Drawings

PROCESS FOR CONTROLLING MOSS AND LIVERWORT

RELATED APPLICATIONS

This is a divisional application of copending U.S. patent application Ser. No. 10/139,164 filed on May 2, 2002 by the inventor of this application.

BACKGROUND OF THE INVENTION

This invention relates to pesticides for agricultural, horticultural including aquaculture and particularly to products that directly kill or impact the life cycle of simple celled organisms such as microscopic insect larvae, algae, fungi, bacteria, mosses, and bryophytes such as liverworts. Pesticides, also known as biocides, are used to control these pests. The pests are commonly found in commercial and agricultural greenhouse, landscapes, nursery fields, storage areas, and aquaculture sites. The invention has applications in all aspects of horticulture and agriculture. Formulation variations can be applied directly to all types of plant, flower and turf tissue without any danger of phytotoxicity when used in accordance with prescribed directions.

Pesticides are an important component of agricultural production throughout the world. Pest control pertains to a wide range of environmental interventions that have their objective to kill or reduce to acceptable levels moss and algae pests, plant pathogens and weed populations. Specific control techniques include chemical, physical and biological control mechanisms. It has been estimated that pests annually destroy about 35% of all food crops before they are harvested and another 10-20% after the food is harvested.

Chemical controls include chemical agent pesticides that include herbicides, for the control of weeds, moss and algaecides for the control of moss and algae pests and fungicides for the control of soil and plant pathogens that include bacteria, fungi and viruses. Herbicides that destroy or inhibit plant growth account for over half of the pesticides that are uses world wide, with 30-35% of pesticide production in the form of moss and algaecides and the balance and the form of fungicides.

All living organisms are composed of cells. The result of biosynthesis is cell growth. Microorganisms live in natural habitats in which their growth is affected by interactions with populations of other microbes, as well as by the physical and chemical characteristics of their environment. Some microbial species can have devastating effects on human beings by causing infectious diseases. A great success of the science of microbiology has been the control of fatal infectious diseases in developed countries. However, these diseases are still important causes of death in less developed parts of the world. Microbes are also important in agriculture and food spoilage.

The growth of bacteria such as *E. coli* depends upon not only the provision of nutrients, but also the existence of appropriate environmental conditions such as temperature, pH, water activity, and aeration. Species differ in the range of these factors within which they will grow.

In general, organisms can grow over a temperature range of 30 to 40 C. However, species differ in range, and four categories have been delineated on this basis. Mesophiles have optimal growth temperatures in the range 20-50 degrees C.; that is, the temperatures most common on the earth's surface or in animals. Psychrophiles have optimal temperatures below 15 C. These organisms are killed by exposure to room temperature. They function at low temperature by having high contents of unsaturated fatty acids in their membranes. These molecules remain fluid at temperatures where membranes containing saturated fatty acids are nonfunctional.

Psychrotrophs can cause spoilage of refrigerated products, such as food or blood. They grow fastest at temperatures above 20 C, and therefore are likely to contaminate these products, but are capable of slow growth at refrigerator temperatures.

Most microbes grow somewhere within the pH range of 5 to 9; most natural environments fall within this range. However, species do exist which grow at pH extremes. Fungi tend to grow at lower pH values than do bacteria.

It is important to control populations of simple celled organisms that affect ornamental and agricultural crops due to the ability of the organisms to inflict major damage to the crops that directly and indirectly cause crop loss. Moss and algae can directly affect crop loss due to the ability of both algae and moss to grow quickly over soil surfaces and prevent the plant from growing. In addition moss and algae also directly affect the aesthetics of the plant, which in the case of ornamental crops such as cut flowers and house plants make the crop unmarketable.

Moss and algae pose indirect problems to the production of plants due to their developing a parasitic relationship with the plant material. Both algae and moss tend to grow on the soil surface thereby denying the plant of nutrients and creating a sometimes-impermeable cap that prevents the plant's root system from getting water.

Most modern day moss control products (mosscides) and algaecides are comprised of long lasting, synthetic compounds that affect the cell structure of simple celled organisms on contact. While these pesticides have proven to be very effective at controlling moss and algae they have also contributed to an unacceptable environmental cycle that directly affects human health and welfare as well as direct and indirect environmental damage. Modern day moss and algaecides primarily work by placing a poison or toxin residue on the surface of plant tissue or by directly spraying the moss and algae pest with the poison compound.

There are several problems that arise from using chemical moss and algaecides and they are as follows:

Resistance: Since traditional moss controls and algaecides work on the principal of chemical toxicity, the moss and algae is capable through genetic mutation of developing a resistance to the toxins that affect it. In the moss and algae world, where generations are produced in the pans of weeks, the problem of genetic resistance is common. Within a very short amount of time, many mosses and algae that were formally susceptible to certain chemical compounds, find that sometimes within the span of a few years, the chemical either does not produce a kill or the dosage must be increased to produce a kill.

This is why moss and algaecide applicators must cycle their applications of different chemical compounds so as not to allow moss and algae they are trying to control to become accustom to any one chemical compound and ultimately to become immune to the chemical. This practice of chemical rotation is both times consuming and expensive, since the applicators must have at minimum three different chemical compounds for various types of moss and algae pests.

Human Toxicity: Most chemical moss controls and algaecides must be used and applied with extreme caution. The applicator must at all times wear special protective personal protection clothing. This includes the use of respirator and eye protection, as well as chemical impervious coveralls and gloves. Since the moss and algaecides produce a toxic residue and are by nature long lasting and complex compounds, over a period of time, direct exposure to moss and algaecides can lead to human health concerns and in some cases direct exposure to certain moss and algaecides can lead to toxic shock and death.

Environmental Damage: Due to the very nature of the moss controls and algaecide that is designed to leave behind a toxic residue on either plant surfaces or in the soil, environmental damage is a direct concern. With the increasing concern over the impact of groundwater by complex pesticide compounds that do not break down into innocuous substances. It has been documented that pesticide compounds have directly impacted groundwater aquifers across the country and become a direct threat to environmental security.

In addition to concerns about groundwater impacts, treatments for moss, algae and other simple cell microorganisms have the capacity to impact non-target organisms within the environment that come into contact with the chemical compounds. These organisms include fish, birds, other non-pest moss and algae, and all forms of animal life. The impact of the insecticide DDT and other chemical treatments ostensibly intended to benefit society while in fact entering the food chain and impacting birds such as the American bald eagle, storks, rainbow trout and others has been well-documented.

SUMMARY OF THE INVENTION

It is an object of the invention to provide a process for controlling simple celled organism such as algae, bacteria, fungi, worts and moss.

Another object of the present invention is to provide a process that is environmentally friendly, does not leave any toxic residue after application, and produces no impact on existing or subsequent generations of human or animal life.

Another object of the present invention is to provide a process that does not impact the health of the user or others and specifically does not affect groundwater aquifers, or require the use of protective clothing.

Still another object of the present invention is to provide a safe method of controlling simple celled organisms by killing the organisms and inhibiting the reproduction of the organisms.

Yet another object of the invention is to provide a method for controlling such simple cell microorganisms that is not vulnerable to mutations of the microorganisms.

It has now been found that these and other objects of the invention are achieved by a process of controlling a wide variety of simple celled pests by applications of various formulations using sodium peroxyhydrate as its principal active ingredient.

Some forms of the pesticide further include at least one other less reactive material which may be selected from the group consisting of lime (calcium oxide), gypsum, and clay. The proportions of the sodium percarbonate and the at least one other less reactive material may be approximately equal by weight or volume.

And some embodiments of the invention the pesticide includes a material selected to control the pH at the area of application and thereby constrain the development of microorganisms. The material selected to control pH at the area of application may be lime.

The invention also includes the process for controlling microorganisms on turf which comprises applying sodium percarbonate and irrigating the turf. Some embodiments of the process in accordance with present invention further include the step of applying a substance to control the pH of the turf and thereby constrain development of additional microorganisms. The sodium percarbonate may be utilized in either a solid form or may be in solution.

The sodium percarbonate may be applied at a rate of at least 1 pound per 1000 square feet. In other forms of the invention the sodium percarbonate is applied as a rate of less than 8 pounds per 1000 square feet.

The invention also includes the process for controlling microorganisms in an aquaculture environment which comprises depositing at least 9 pounds of sodium percarbonate per million gallons of water in the aquaculture environment.

In other embodiments of the invention the process for controlling microorganisms in an aquaculture environment includes depositing less than 52 pounds of sodium percarbonate per million gallons of water.

DESCRIPTION OF THE PREFERRED EMBODIMENT

Because of the problems associated with the use of traditional chemical moss and algaecides a need exists for a safe method to control moss and algae pests commonly found in commercial horticulture and agriculture. As used herein the term "controlled" as used herein means a reduction in the overall population of the organisms.

Formulations of sodium percarbonate (also known as sodium peroxyhydrate) combination with an equal amount of soda ash either by weight or by volume can be used to actively control existing populations of simple celled organisms that reside on the soil surfaces or on the surfaces of container crops. The effective range of sodium percarbonate/soda ash combination can range from 2 to 8 pounds per 1000 square feet. Treatment of soil surfaces can be achieved by spreading the granular formulation on soil surfaces by hand, or by mechanical spreaders. The formulation of sodium percarbonate and soda ash is water-soluble and may be diluted in water and applied through spray equipment to soil surfaces.

Additionally, the sodium percarbonate soda ash formulation may be applied to bodies of water, such as those used for aquaculture, to treat and control filamentous algae, pathogenic bacteria and fungi. Effective concentrations can range from 30-150 pounds of sodium percarbonate per acre-foot of water or 9-500 pounds per million gallons of water. This embodiment of the invention has application to treatment of bodies of water for aquaculture as well as bodies of water for other applications.

Formulations of sodium percarbonate and soda ash when applied to soil and incorporated into the first six inches of soil actively control and inhibit the germination of weed seeds from germinating by directly affecting the pH of the soil. Effective rates range between 4 and 8 lbs per 1000 square feet of soil surface area.

The preferred formulation includes a combination of sodium percarbonate and at least one of various materials such as lime (calcium oxide), gypsum, clay and/or other less reactive material to control simple celled organisms on the surfaces such as algae, moss, bacterial, fungal and other organisms and insect larvae.

The composition in accordance with the preferred embodiment includes sodium percarbonate in combination with various combinations of soda ash, lime, gypsum, clay and a variety of other inert materials. The choice among the group consisting of soda ash, lime, gypsum, clay and a variety of other inert materials depends on the pH of the surface or body to be treated. Generally formulation used to actively kill simple celled organisms in the presence of growing plant material will use inert materials such as lime, clay that do not exhibit a pH higher than 7.5. For those applications that are made to control simple celled organisms where impact on growing plant materials is not a factor, then inert materials such as soda ash with a high residual pH are used to help inhibit the further growth of microorganisms.

EXAMPLE 1

A formulation of sodium percarbonate and lime formulated in a 50-50 by weight mixture was applied to bent grass turf to kill and control silver tread moss growing on the soil surfaces. The approach is preferable to prevent the moss from competing with the turf grass and making the putting green unsightly and unplayable. The formulation was applied by a drop spread calibrated to apply 4 pounds of material per 1000 square feet of area. The formulation was deposited on the turf surface and them was lightly irrigated to activate the sodium percarbonate. Results were observed with 48 hours of initial application indicating the moss was affected and exhibited a color change from a health green to a rust color, which indicated control. One week latter the turf was treated again and the moss was eradicated.

EXAMPLE 2

A putting green having bent grass and silver tread moss was treated with a formulation of sodium percarbonate and lime formulated in a 50-50 by weight mixture was applied to putting green to kill and control the silver tread moss growing on the soil surfaces. The process was required because the moss was competing with the turf grass and making the putting green unsightly and unplayable. The formulation was applied by a drop spreader calibrated to apply 8 pounds of material per 1000 square feet of area. The formulation was deposited on the turf surface and them was lightly irrigated to activate the sodium percarbonate. Results were observed with 48 hours of initial application indicating the moss was affected and exhibited a color change from a health green to a rust color, which indicated control. One week later the moss that was determined to be free of moss.

EXAMPLE 3

A formulation of sodium percarbonate and Lime formulated in a 50-50 by weight mixture was applied to a bent grass turf to kill and control filamentous algae growing on the soil surfaces. The application was made by applying 6 pounds per 1000 square feet with a mechanical drop spreader. The formulation was not activated due to the high degree of latent moisture on the turf. Within 24 hours of application the algae turned a black color and within 48 hours was dead.

EXAMPLE 4

A formulation using 50% sodium percarbonate and 50% lime by weight was used to control liverwort growing on the surfaces of nursery container in which woody ornamental plants were growing. Liverwort is a bryophyte organism that resembles a mushroom. The liverwort grows on the surface of the container, creating an impermeable surface under which the plant is prevented from receiving water due to the liverwort covering the soil surface to form an impermeable plug.

One-eighth of a teaspoon of the formulation was uniformly distributed over the top surface of a 3-gallon pot containing woody ornamental plants. The plants were irrigated with water to thoroughly wet the root zone after application. The liverwort began to show signed of desiccation after 48 hours of application. A subsequent application was made five days later and the treated plants had a 95% reduction in liverwort.

Although the invention has been described in terms of a sodium percarbonate in a solid form it will be understood that in various forms of the invention the sodium percarbonate may be in solution.

The invention has been described with reference to the preferred embodiment. Persons skilled in the art of such inventions may upon exposure to the teachings herein, conceive other variations such variations are deemed to be encompassed by the disclosure, the invention being delimited only by the following claims.

What is claimed is:

1. A process for eradicating moss which comprises:
   applying sodium percarbonate; and
   irrigating the moss.

2. A process for eradicating moss in accordance with claim 1 further including applying lime to control the pH of the moss and thereby constrain development of additional moss and said sodium percarbonate is a solid material.

3. A process for eradicating moss in accordance with claim 1 further including applying lime to control the pH of the moss and thereby constrain development of additional moss and said sodium percarbonate is in solution.

4. A process for eradicating moss in accordance with claim 2 further including applying lime to control the pH of the moss and thereby constrain development of additional moss and wherein said sodium percarbonate is applied at a rate of at least 1 pound per 1000 square feet.

5. A process for eradicating moss in accordance with claim 3 further including applying lime to control the pH of the moss and thereby constrain development of additional moss and said sodium percarbonate is applied at a rate of at least 1 pound per 1000 square feet.

6. A process for eradicating moss in accordance with claim 2 further including applying lime to control the pH of the moss and thereby constrain development of additional moss and said sodium percarbonate is applied as a rate of less than 8 pounds per 1000 square feet.

7. A process for eradicating moss in accordance with claim 4 further including applying lime to control the pH of the moss and thereby constrain development of additional moss and said sodium percarbonate is applied at a rate of less than 8 pounds per 1000 square feet.

8. A process for eradicating moss which comprises:
   applying sodium percarbonate,
   applying a soda ash to control the pH of the moss and thereby constrain development of additional microorganisms, and
   irrigating the moss.

9. A process for eradicating moss in accordance with claim 8 wherein said sodium percarbonate is a solid material.

10. A process for eradicating moss in accordance with claim 8 wherein said sodium percarbonate is in solution.

11. A process for eradicating moss in accordance with claim 8 wherein said sodium percarbonate is applied at a rate of at least 1 pound per 1000 square feet.

12. A process for eradicating moss in accordance with claim 10 wherein said sodium percarbonate is applied at a rate of at least 1 pound per 1000 square feet.

13. A process for eradicating moss in accordance with claim 9 three wherein said sodium percarbonate is applied as a rate of less than 8 pounds per 1000 square feet.

14. A process for eradicating moss in accordance with claim 10 wherein said sodium percarbonate is applied at a rate of less than 8 pounds per 1000 square feet.

15. A process for eradicating moss which comprises:
applying sodium percarbonate;
irrigating the moss; and
further including applying a substance having a pH less than 7.5 to control the pH of the moss and thereby constrain development of additional microorganisms.

16. A process for eradicating moss in accordance with claim 15 wherein said sodium percarbonate is a solid material.

17. A process for eradicating moss in accordance with claim 15 wherein said sodium percarbonate is in solution.

18. A process for eradicating moss in accordance with claim 15 wherein said sodium percarbonate is applied at a rate of at least 1 pound per 1000 square feet.

19. A process for eradicating moss in accordance with claim 15 wherein said sodium percarbonate is applied as a rate of less than 8 pounds per 1000 square feet.

20. A process for desiccating liverwort and moss which comprises:
applying sodium percarbonate, and
irrigating the moss and liverwort.

* * * * *